(12) United States Patent
Wehmeier et al.

(10) Patent No.: US 8,245,566 B2
(45) Date of Patent: Aug. 21, 2012

(54) PROCEDURE AND DEVICE FOR DIAGNOSING AN EXHAUST GAS PROBE

(75) Inventors: Kersten Wehmeier, Ludwigsburg (DE); Ronaldi Rusli, Korntal-Muenchingen (DE); Andreas Koring, Reutlingen (DE); Richard Hotzel, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 439 days.

(21) Appl. No.: 12/571,587

(22) Filed: Oct. 1, 2009

(65) Prior Publication Data

US 2010/0083743 A1 Apr. 8, 2010

(30) Foreign Application Priority Data

Oct. 1, 2008 (DE) .......................... 10 2008 042 549

(51) Int. Cl.
*G01M 15/10* (2006.01)

(52) U.S. Cl. .................................... 73/114.72

(58) Field of Classification Search ................. 73/23.32, 73/114.72
See application file for complete search history.

(56) References Cited

U.S. PATENT DOCUMENTS

| | | | | |
|---|---|---|---|---|
| 6,131,446 | A * | 10/2000 | Schnaibel et al. | 73/114.73 |
| 6,961,653 | B2 * | 11/2005 | Maki | 701/109 |
| 7,021,300 | B2 * | 4/2006 | Maki et al. | 123/688 |
| 7,481,104 | B2 | 1/2009 | Schmaibel et al. | |
| 7,874,285 | B2 * | 1/2011 | Barnikow et al. | 123/688 |
| 7,934,420 | B2 * | 5/2011 | Kama et al. | 73/114.69 |
| 8,047,064 | B2 * | 11/2011 | Iwazaki et al. | 73/114.72 |
| 2005/0138917 | A1 * | 6/2005 | Maki | 60/277 |
| 2007/0119242 | A1 * | 5/2007 | Buck et al. | 73/118.1 |

FOREIGN PATENT DOCUMENTS

DE 102 60 721 7/2004

* cited by examiner

*Primary Examiner* — Freddie Kirkland III
*(74) Attorney, Agent, or Firm* — Merchant & Gould P.C.

(57) ABSTRACT

A procedure and device for diagnosing the increasing speed and the dead time of an exhaust gas probe includes carrying out the diagnosis by comparing a modeled and a measured signal after a default change of a fuel air ratio of an air fuel mixture that is supplied to a combustion engine. The signal is an output signal of the exhaust gas probe or a modeled or measured signal that is derived from the output signal. The device for diagnosing the velocity and the dead time of an exhaust gas probe also includes a comparing unit for comparing the modeled signal with the measured signal for diagnosing the velocity and the dead time of the exhaust gas probe after a default change of a fuel air ratio of an air fuel mixture that is supplied to the combustion engine.

15 Claims, 1 Drawing Sheet

PROCEDURE AND DEVICE FOR DIAGNOSING AN EXHAUST GAS PROBE

This application is claims benefit of Serial No. 10 2008 042 549.4, filed 1 Oct. 2008 in Germany and which application is incorporated herein by reference. To the extent appropriate, a claim of priority is made to the above disclosed application.

BACKGROUND

The invention relates to a procedure for diagnosing the velocity and the dead time of an exhaust gas probe, which is arranged in an exhaust gas duct of a combustion engine, whereby the diagnosis is carried out on the basis of a comparison of a modeled and a measured signal after a default change of a fuel air ratio of an air fuel mixture that is supplied to a combustion engine and whereby the signal is an output signal of the exhaust gas probe or a modeled or measured signal that is derived from the output signal.

SUMMARY

The invention furthermore relates to a procedure for determining the dead time of an exhaust gas probe, which is arranged in an exhaust gas duct of a combustion engine, whereby the diagnosis is carried out on the basis of a comparison of a modeled and a measured signal after a default change of a fuel air ratio of an air fuel mixture that is supplied to a combustion engine and whereby the signal is an output signal of the exhaust gas probe or a modeled or measured signal that is derived from the output signal.

The invention furthermore relates to a device for diagnosing the velocity and the dead time of an exhaust gas probe, which is arranged in an exhaust gas duct of a combustion engine, with a calculation model for calculating a modeled signal and measuring means for determining a measured signal, whereby the signal is a modeled or measured output signal of the exhaust gas probe or a modeled or measured signal that is derived from the output signal, with a comparing unit for comparing the modeled signal with the measured signal for diagnosing the velocity and the dead time of the exhaust gas probe after a default change of a fuel air ratio of an air fuel mixture that is supplied to the combustion engine.

For optimizing pollutant emission and the exhaust gas after treatment different types of exhaust gas probes are used in modern combustion engines for determining the composition of the exhaust gas and for controlling the combustion engine. They can for example be lambda probes for determining the oxygen content of the exhaust gas and deriving from that for regulating the air fuel mixture that is supplied to the combustion engine or NOx-sensors.

With the aid of the lambda probe the air and fuel supply of the combustion engine is regulated by a lambda control loop in such a way that a composition of the exhaust gas is achieved that is optimal for the exhaust gas after treatment by the catalytic converters that are contained in the exhaust gas duct of the combustion engine. At Otto engines for example a lambda of preferably 1 is regulated, thus a stoichiometric relation of air and fuel. The pollutant emission of the combustion engine can thereby be minimized.

Different types of lambda probes are used. At the two-point lambda probe, also called jump probe or Nernst probe, the characteristic line provides a jumpy drop at lambda=1. It basically allows therefore only the distinction between rich exhaust gas during operation of the combustion engine with fuel surplus and lean exhaust gas during operation with air surplus.

A wide band lambda probe, also called steady or linear lambda probe, allows the measuring of the lambda value in the exhaust gas in a wide area around lambda=1. Therefore a combustion engine can also be for example regulated to a lean operation with air surplus.

A fast regulation of the exhaust gas composition is significant for the low-emission operation of the combustion engine, for example to a default lambda value. This applies in particular also for combustion engines with one-cylinder regulation, where the air fuel mixture is individually adjusted for each single cylinder of the combustion engine based on the signal of the common lambda probe. The lambda measurement has therefore be carried out with a high timely resolution, in order to be able to determine the composition of the consecutive exhaust gas volumes of the different cylinders that arrive at the lambda probe and to assign them to the corresponding cylinder.

Besides the chosen regulating parameters of the lambda control loop and the distance parameters the dynamic of the lambda probe determines the speed of the control loop. In mint condition the dynamic of lambda probes is thereby also sufficient for regulating a single cylinder regulation with a common lambda probe for all cylinders in a common exhaust gas duct. Due ageing effect the dynamic characteristics of the lambda probes can change in such a way that the reaction speed of the lambda probe is not sufficient anymore for determining the exhaust gas composition, which causes an increased pollutant emission. If the pollutant emission is outside the statutory provisions the lacking dynamic of the lambda probe can be determined in the range of the on-board diagnosis and a corresponding error message is provided.

At a lambda probe, in particular a wide band lambda probe a change of the increasing speed or the dead time can take place asymmetrically, thus varyingly strong for a change of the air fuel mixture that is supplied to the combustion engine from lean to rich and from rich to lean. Such an asymmetrical slowdown has often more negative effects on the pollutant emissions than a symmetric slowdown of the same dimension. This is based on the fact that asymmetric slowdowns shift the lambda average value that is adjusted by the lambda regulation. If the lambda average value is shifted by a rich-lean slowdown of the lambda probe to lean a three-way catalytic converter that is arranged in the exhaust gas duct for example cannot convert the nitric oxides sufficiently anymore. If the lambda average value is on the other hand shifted by a lean-rich slowdown of the lambda probe to rich the three-way catalytic converter cannot convert carbon monoxide and eventually also hydrocarbon sufficiently anymore. In several countries the detection of an asymmetric slowdown of the lambda probe has therefore to be determined in the range of the on-board diagnosis.

DE 102 60 721 A1 describes a procedure for diagnosing the dynamic characteristics of a lambda probe, which is at least temporarily used for a cylinder individual lambda regulation, as well as a related diagnosing device. It is thereby provided that at least one manipulated variable of the lambda regulation is detected and compared to a default maximum threshold value and that the dynamic behavior of the lambda probe with regard to the usability for a cylinder individual lambda regulation is evaluated as not sufficient in the case of an exceeding of the maximum threshold value. The dynamic characteristics of the lambda probe can be detected from the single cylinder regulation itself because the cylinder individual regulators diverge at an insufficient dynamic of the lambda probe. Furthermore a test function can be provided with a targeted disruption or detune of the actual lambda value.

Further diagnosing procedures for determining the dynamic characteristics of lambda probes are known. Thus a measured lambda signal can for example be compared to an expected lambda signal after fuel jumps of a known height. The expected lambda signal is correspondingly calculated with a known procedure by a distance model. The fuel jumps are thereby specified by a modulation of the fuel correcting factor of the lambda regulation. The expected and the measured lambda signal are made zero-mean by a high pass filtering and eventually freed from noise by a low pass filtering. For each of the signals that are filtered this way an integration above a certain time is started after a fuel jump at the point of time when the lambda signal is passing through zero. Subsequently the integral of the filtered and measured lambda signal is compared to the integral of the filtered and expected lambda signal and a single result of the dynamic diagnosis is calculated from the comparison. The single results are separately created for rich-lean and for lean-rich fuel jumps. In order to compensate the scattering of the single results, discrete filters are used. An error of the lambda probe is detected if one of the filter values lies below a threshold value after a certain number of single results.

A disadvantage of many familiar procedures is though that only a change of the time constant of the lambda probe can be detected but not a pure dead time in the probe signal. It is for example not possible to detected a pure dead time with a comparison between the measured and expected lambda signal at a periodical excitation because there is no possibility to distinguish whether an observed reaction in the measured lambda signal is based on the excitation of directly previous period or on an earlier period.

It is therefore the task of the invention to provide a procedure, which enables a reliable diagnosis of the increasing speed and the dead time of exhaust gas sensors, and it is the task of the invention to provide a procedure, which enables a reliable diagnosis of the dead time of exhaust gas sensors.

It is furthermore the task of the invention to provide a device, which enables a reliable diagnosis of the increasing speed and the dead time of exhaust gas sensors.

ADVANTAGES OF THE INVENTION

The task of the invention that relates to the first procedure for diagnosing the increasing speed and the dead time of an exhaust gas probe is thereby solved, in that a first extreme value is determined in the course of the modeled signal and that a first point of time and a first starting value are determined if the modeled signal deviates by a default amount from the first extreme value, in that a second extreme value in the course of the measured signal is determined and in that a second point of time and a second starting value are determined, if the measured signal deviates from the second extreme value by a pre-determined amount, in that a first integral is created over a certain period of time, beginning at the first point of time above the different between the first starting value and the modeled signal and in that a second integral is created over a second period of time, beginning at the second point of time, above the difference between the second starting value and the measured signal, in that the second period of time is equal to the pre-determined period of time or that the end of the second period of time related to the point of time of the change of the fuel air ratio or related to a first point of time is determined and in that from a quantitative comparison between the first integral and the second integral a quantitative comparative value is created, which indicates the increasing speed and/or the dead time of the exhaust gas probe.

The extreme values in the signals are develop as maximum values or minimum values in the time course of the signals depending on the direction of the default change of the fuel air ratio from rich to lean or lean to rich. Due to the flat curve course in the area of the extreme values the timely determination of the extreme values is possible only inaccurately at the modeled as well as at the measured signal. A point of time after an extreme value, at which the signal has changed by a default amount from the value of the extreme value to a registered starting value, can be determined very accurately due to the steep curve course and is therefore suitable as starting point for the integration that has to be carried out.

The first integration over the default period of time and over the difference between the modeled and the measured signal and the associated first starting value deliver a value, which is characteristic for the default increasing speed of the exhaust gas probe. If the second period of time as integration period for the difference between the measured signal and the associated second starting value is chosen to be equal to default period of time, the increasing speed of the exhaust gas probe can be indicated from the quantitative comparison of the first and the second integral. A slowed down exhaust gas probe causes a comparatively smaller second integral, which shows up in the created quantitative comparative value. Because the points of time of the start of the integration are not coupled to a determined point of time but variably to the signal courses, the increasing speed of the exhaust gas probe can be determined independent of the influences of a dead time of the exhaust gas probe that changes due to ageing.

If the end of the integration of the measured signal is determined firmly to a point of time that is not connected to the signal course of the measured signal in such a way, that the integration time of the measured signal is shorter than of the modeled signal, the quantitative comparison of the first and the second integral delivers information about the increasing speed as well as the dead time of the exhaust gas probe. The second integral is than the shorter the slower the exhaust gas probe reacts due to a reduced increasing speed and the later the exhaust gas probe reacts upon the change of the fuel air ratio due to a extended dead time. If the increasing speed of the exhaust gas probe is known due to previous measurement with the same integration time periods the dead time can be determined separately from the comparison of the integrals at a shortened second period of time.

The procedure enables therefore the secure determination of the increasing speed as well as of the dead time of exhaust gas probes.

If it is provided that the quantitative comparative value is determined by creating a difference or a quotient between the first integral and the second integral or between the second integral and the first integral, deviations between the first integral and the second integral can be described in a characteristic value that can be simply created and evaluated.

According to a preferred embodiment it can be provided that the previously determined period of time depends on the operating parameters of the combustion engine. The exhaust gas current, exhaust gas composition or the operating parameters of the exhaust gas probe, as for example the temperature of the exhaust gas probe, depend on the operating parameters of the combustion engine. All those parameters have an impact on the signal course of the exhaust gas probe. By adjusting the pre-determined period of time to the operating parameters of the combustion engine this influence can be considered.

According to a further preferred embodiment it can be provided that the end of the second period of time related to the point of time of the change of the fuel air ratio or related to the first point of time is determined depending on the operating parameters of the combustion engine. The relation of the end of the integration time period of the measured signal to the point of time of the change of the fuel air ratio as well as the relation to the first point of time as starting point of the first integration of the modeled signal course enable the described determination of the dead time of the exhaust gas probe. The consideration of the operating parameters of the combustion engine is useful because it has an effect on the dead time of the exhaust gas probe.

The task of the invention that concerns the second procedure for determining the dead time of an exhaust gas probes thereby solved, in that a first extreme value in the course of the modeled signal is determined and in that a first point of time is determined, if the modeled signal deviates by a pre-determined amount from the first extreme value, in that a second extreme value is determined in the course of the measured signal and in that a second point of time is determined, if the measured signal deviates by a pre-determined amount from the second extreme value and in that the dead time of the exhaust gas probe is determined from the difference between the second point of time and the first point of time.

The advantage here is also that the points of time that are compared to each other can be determined very accurately due to the steep curve course in the areas of the signal curves that are defined by the default change of the amount of the signals.

An exhaust gas probe that reacts delayed due to a higher dead time will cause a timely delayed reaction upon a change of the fuel air ratio. The measured course of the signal is correspondingly shifted to bigger times. By determining the first point of time and the second point of time relatively to the modeled and measured signal course the delay of the measured signal course can be directly determined in comparison to the modeled signal course and therefore also the dead time of the exhaust gas probe by comparing the first and the second point of time.

If it is provided that the increasing speed and the dead time are determined and separately evaluated after a change of the fuel air ratio from a lean to rich mixture and from a rich to a lean mixture, an asymmetrically slowed down increasing speed or an asymmetrically extended dead time of the exhaust gas probe can be determined. Such asymmetrical slowdowns of the same type can cause a more negative effect on the pollutant emission of the combustion engine.

A clear determination of an improperly slowed down exhaust gas probe can be thereby achieved, in that a malfunctioning exhaust gas probe is assumed, if the quantitative comparative value exceeds or falls below a default first threshold value or if the dead time exceeds a default second threshold value. The determination of the first threshold value as proper maximum value or prober minimum value is thereby depending on the way how the quantitative comparative value is created, for example as a quotient between the first integral to the second integral or as quotient between the second integral to the first integral.

By evaluating the single results with discrete filters the security of the statement about whether the increasing speed or the dead time of the exhaust gas probe is insufficient, can be increased. Therefore it can be provided that a malfunctioning exhaust gas probe is assumed if the quantitative comparative value or the average value of the quantitative comparative value exceeds or falls below the first default threshold value or if the dead times or the average value of the dead times exceed the default second threshold value in several consecutive determinations.

If it is provided that an intervention into the air fuel mixture is determined from the difference between the dead times at change of the fuel air ratio from a lean to a rich mixture or from a rich to a lean mixture and/or from the difference between the amounts of the quantitative comparative values at a change of the fuel air ratio from a lean to a rich mixture and a change from a rich to a lean mixture, at least one part of the negative effects of an asymmetrically slowed down exhaust gas probe can be balanced. At a wide band lambda probe that is for example used for a lambda regulation an asymmetric slowdown of the wide band lambda probe can therefore cause a shifting of the lambda average value that is adjusted by the lambda regulation with a correspondingly negative effect on the exhaust gas after treatment by catalytic converters that are provided in the exhaust gas duct for this purpose. By a corresponding adjustment of the lambda regulation to the measured asymmetrical slowdown of the wide band lambda probe the lambda average value can be regulated back to the default value and thereby the pollutant emission can be improved.

The influence of an asymmetrically slowed down exhaust gas probe can be thereby balanced, in that the air fuel mixture that is supplied to the combustion engine is made richer, if the quantitative comparative value of the integrals allows the assumption of a bigger deviation of the integral at a change of the fuel air ratio from a rich to a lean mixture than at a change of the fuel air ratio from a lean to a rich mixture and in that the air fuel mixture is made more lean, if the quantitative comparative value of the integrals allows the assumption of a bigger deviation of the integral at a change of the fuel air ratio from a lean to a rich mixture than at a change of the fuel air ratio from a rich to a lean mixture.

A wrongly slowed down exhaust gas probe can be signalized to the operator of the combustion engine and/or registered in an error memory. The registration in an error memory can be read during a visit of an auto shop and upon that the malfunctioning exhaust gas probe can be permanently exchanged.

According to a preferred embodiment of the invention it can be provided that the evaluation takes place on the basis of the inverted lambda signal of a wide band lambda probe. The use of the inverted lambda signal instead of the lambda signal itself is advantageously because the raw value of the lambda probe signal is proportional to the inverted lambda signal.

The procedure can be preferably applied for the diagnosis of a wide band lambda probe or for the diagnosis of a nitric oxide sensor.

The task of the invention that relates to the device is thereby solved, in that a tracker is provided for determining a first extreme value, a first starting value and a first point of time in the course of the modeled signal, in that a second tracker is provided for determining a second extreme value, a second starting value and a second point of time in the course of the measured signal, in that a first integrator is provided for creating a first integral by integrating the difference of the modeled signal to the first starting value, beginning at the first point of time over a pre-determined period of time and in that a second integrator is provided for creating an integral by integrating the difference of the measured signal to the second starting value, beginning at the second point of time over a second period of time, and in that the first point of time and the second point of time as well as the first integral and the second integral are supplied to a comparing unit.

The device enables thus the creation and the comparison of the integrals for determining the increasing speed and the dead time of the exhaust gas probe, as it is already stated for the procedure. The device enables furthermore the determination and the comparison of the first point of time and the second point of time, whose difference creates the dead time of the exhaust gas probe.

According to a particularly preferred embodiment of the invention it is provided that the function of the calculation model, the trackers, the integrators and the comparing unit are construed within a motor electronic as soft and/or hardware solution. The function can therefore be integrated in motor or control electronics that are already provided in modern combustion engines.

BRIEF DESCRIPTION OF THE DRAWINGS

The invention is subsequently further explained with the aid of the embodiment that is illustrated in the figures. It is shown.

DETAILED DESCRIPTION

Figure 1:
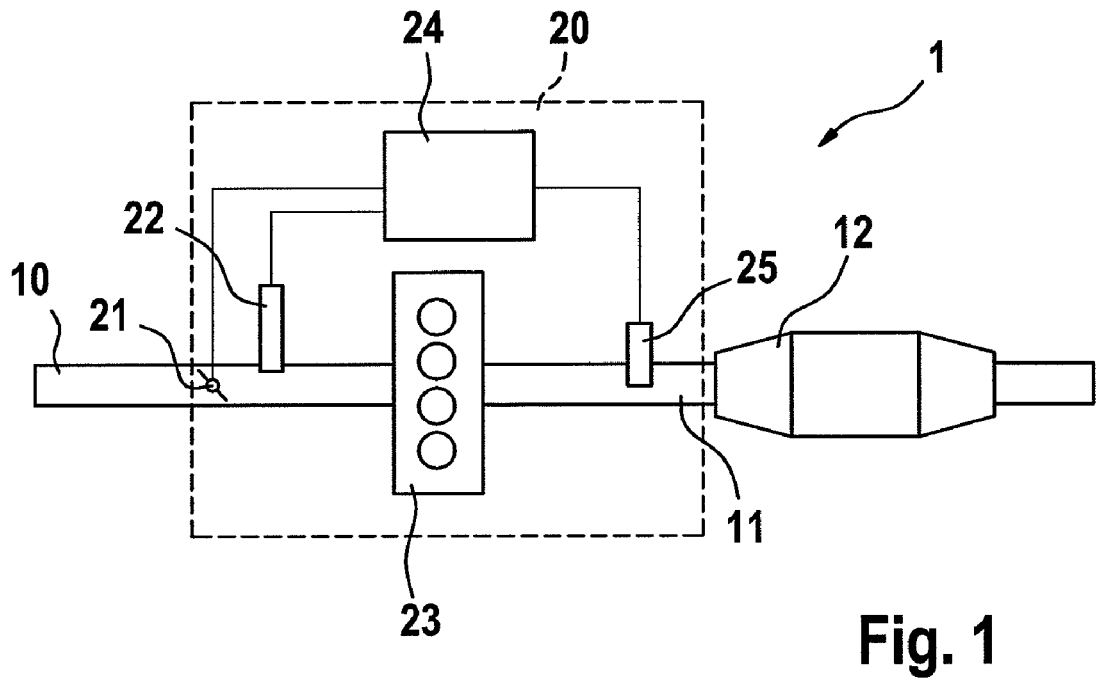
FIG. 1 is a schematic illustration of the technical environment, in which the procedure is carried out

FIG. 1 shows the technical environment in a schematic illustration, in which the procedure can be used. The illustration is thereby limited to the components that are required for explaining the invention.

Illustrated is a combustion engine 1 with an exhaust gas probe in the form of a wide band lambda probe.

The combustion engine 1 consists of an engine block 23 with four cylinders. The engine block 23 is supplied with fresh air over a supply duct 10 and with fuel over a fuel metering device 22. In the supply duct 10 is a throttle valve 21 for adjusting the supplied air quantity. An exhaust gas duct 11 is arranged after the engine block 23, in which the wide band lambda probe 25 and catalytic converter 12 are arranged in the direction of the current of the exhaust gas.

The throttle valve 21, the fuel metering device 22 and the wide band lambda probe 25 are connected to the motor electronic 24. Together with the engine block 23 they create a REGELKREIS 20 for the lambda regulation. The regulation algorithm is thereby stored in the motor electronic 24.

For the normal operation of the combustion engine 1 a linear lambda regulation algorithm is provided in the motor electronic 24. The wide band lambda probe 25 determines the oxygen content in the exhaust gas and produces a corresponding output signal, which is supplied to the motor electronic 24. It creates then thereof regulator correcting variables for the fuel metering device 22 and the throttle valve 21 for adjusting the supplied air quantity in such a way that the combustion engine 1 is operated with a default lambda, thus with a default air fuel ratio. For an optimized exhaust gas after treatment in the catalytic converter 12 that is construed as three-way catalytic converter an operation is provided at a lambda of 1.

A slowdown of the reaction time of the wide band lambda probe 25 influences the lambda regulation and causes an increased pollutant emission of the combustion engine 1. Statutory provisions require complying with threshold values at the pollutant emission, which requires a controlling of the increasing speed and dead time of the wide band lambda probe 25 that depend on ageing.

The slowdown of the wide band lambda probe 25 occurs partially asymmetrically, which means that the reaction speed of the exhaust gas probe is different for the change of the fuel air ratio from rich to lean (rich-lean slowdown) and from lean to rich (lean-rich slowdown). Such an asymmetric slowdown has often a more negative effect on the pollutant emission than symmetric slowdowns of the same dimension. The reason for that is that asymmetric slowdowns shift the lambda average value that is adjusted by the lambda regulation. If the average value is shifted to lean by a rich-lean slowdown, the three-way catalytic converter cannot convert nitric oxides sufficiently anymore. If the average value is shifted to rich by a lean-rich slowdown of the wide band lambda probe 25, the three-way catalytic converter will not be able to convert carbon monoxide and eventually hydrocarbons sufficiently anymore.

Figure 2:
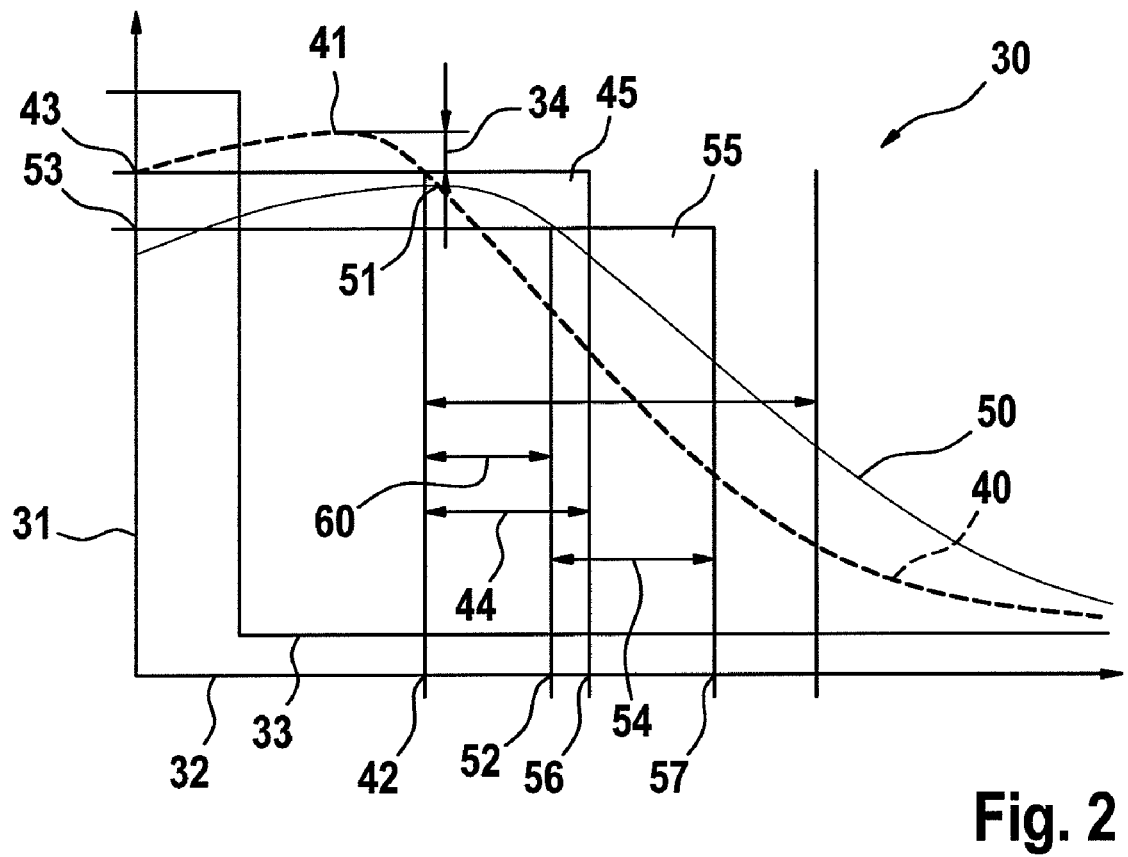
FIG. 2 is a diagram with the time course of a modeled and a measured signal.

FIG. 2 shows a diagram 30 with the time course of a modeled signal 40 and a measured signal 50 of the wide band lambda probe 25 that is shown in FIG. 1. The procedure can however also be applied with different exhaust gas probes, for example a NOx sensor.

The signals 40, 50 are listed as inverted lambda values opposed to a signal axis 31 and a time axis 32. The course of the fuel air ratio 33 that is supplied to the combustion engine 1 is furthermore shown.

The modeled signal 40 is assigned to a first extreme value 41 and a value pair consisting of a first point of time 42 and a first starting value 43. The space, which is spanned by the default period of time 44 and the modeled signal 40 illustrates graphically a first integral 45.

Correspondingly the measured signal 50 is assigned to a second extreme value 51 and a value pair consisting of a second point of time 52 and a second starting value 53. The area, which is spanned by a second period of time 54 and the measured signal 50, graphically illustrates a second integral 55. The end 56 of the second period of time 54 is marked.

The procedure is based on the comparison of the modeled signal 40 and the measured signal 50 after a jump in a familiar height in the fuel air ratio 33. The change of the fuel air ratio 33 is reached by fuel jumps of a defined height.

The calculation of the modeled signal 40 takes place with the aid of a distance model assuming an intact wide band lambda probe 25.

The change of the fuel air ratio 33 takes place in the shown embodiment according to the inverted illustration from rich to lean, thus by a jerky reduction of the fuel amount that is supplied to the combustion engine 1 by a known amount. The evaluation of the inverted lambda signals is advantageous for the diagnosis of wide band lambda probes 25, because the raw value of the lambda probe signal is proportional to the inverted lambda. Due to the jump in the fuel air ratio 33 the first extreme value 41 and the second extreme value 52 are created as maximum values. The evaluation can also be carried out for a jerky change of the fuel air ratio 33 from lean to rich. The extreme values 41, 51 create then minimum values in the signal courses.

After the jump in the fuel air ratio 33 the rotating maximum is determined as first extreme value 41 of the modeled signal 40. The signal course is further tracked until the modeled signal 40 has fallen by a pre-determined value 34 below the maximum of the first extreme value 41 down to the starting value 43. From the now reached first point of time 42 the first integral 45 is created by a timely integration of the difference of the modeled signal 40 and the first starting value 43 over the default period of time 44. The duration of the default period of time 44 is selected depending on the current operating parameters of the combustion engine 1.

The evaluation of the measured signal 50 after the jump in the fuel air ratio 33 takes place correspondingly. At first the rotating maximum is determined as second extreme value 52 of the measured signal 50. Subsequently the signal course is further tracked until the measured signal 50 has fallen down by the same pre-determined value 34 as the modeled signal 40 below the maximum of the second extreme value 51 to the second starting value 53. From the now reached point of time 52 for creating the second integral 55 a timely integration of the difference of the measured signal 50 and the second starting value 53 over the second period of time 54, which corresponds with the default period of time 44 that is shown in the embodiment, is also carried out.

The time between the first point of time 42 in the modeled signal 40 and the second point of time 52 in the measured signal 50 is taken as dead time 60 of the wide band lambda probe 25 for a change of the fuel air ratio 33 from rich to lean. As it has already been mentioned a corresponding evaluation is also carried out for the jerky change of the fuel air ratio 33 from lean to rich. In doing so deviations of the dead time 60 from default values as well as differences of the dead times 60 can be determined depending on the direction of the change of the fuel air ratio 33 from rich to lean or from lean to rich.

The second integral 55 of the measured signal 50 provides information about the increasing speed of the wide band lambda probe 25. The smaller the second integral 55 gets compared to the first integral 45 of the modeled signal course 40, the more the wide band lambda probe 25 is slowed down to the default value. The evaluation here can also be carried out according to the described procedure for a jump of the fuel air ratio from rich to lean and from lean to rich, so that also asymmetrical changes of the increasing speed of the wide band lambda probe 25 can be detected.

The deviation between the first integral 45 and the second integral 55 can be described by a quantitative comparative value. That can be created by a quantitative comparison of the two integrals 45, 55, for example by calculating the difference or the quotient between the first integral 45 and the second integral 55 or between the second integral 55 and the first integral 45. The quantitative comparative value can be simply evaluated in the motor electronic 24 that is shown in FIG. 1

For the end 56 of the second period of time 54 a maximum point of time 57 that depends on operating points is determined. This maximum point of time 57 is related to the first point of time 42, but can also for example be related to the point of time of the jump of the fuel air ratio 33. The latest proper end 56 of the second period of time 54 is limited to the maximum point of time 57. If the reaction of the measured signal 50 takes place due to a strongly extended dead time 60 of the wide band lambda probe 25 occurs very ate the curve of the measured signal 50 shifts over to longer times. The second point of time 54, thus the integration time of the measured signal 50, is then ended at the maximum point of time 57, which causes a small second integral 55. In doing so also pure dead times 60 in the measured signal 50 of the wide band lambda probe 25 cause small integral values. The value of the second integral 55 is then a measure for the increasing speed of the wide band lambda probe 25 as well as for the dead time 60.

The dead time 60 as well as the increasing speed of the wide band lambda probe 25 are determined for a jump of the fuel air ratio 33 from lean to rich and from rich to lean. A slowed down wide band lambda probe 25 is detected if the specific dead time 60 lies above or the increasing speed, determined from the second integral 55 compared to the first integral 45 of the modeled signal 40, lies below a default threshold value. Therefore a discrete filter is calculated for the dead time 60 as well as for the quantitative comparative values of the integrals 45, 55, in which the dead times 60 and the quantitative comparative values are entered as input values and whose output values are considered as test results that are free from scatterings.

In order to compensate the effects of an asymmetrical slowdown of the wide band lambda probe 25 and the pollutant emission of the combustion engine 1, an intervention of the adjusted fuel air ratio 33 is created at differences between the lean-rich and the rich-lean diagnose results. If a lower dynamic of the wide band lambda probe 25 occurs in the rich-lean direction than in the lean-rich direction, the fuel air ratio 33 is increased, thus made richer. If a lower dynamic occurs in the lean-rich direction than in rich-lean direction the fuel air ratio 33 is reduced, thus made leaner.

The procedure allows therefore the detection of dynamic error at exhaust gas probes, which effect the increasing speed and thus the time constant of the exhaust gas probe, like such that effect the dead time 60 in the probe signal. Furthermore separate diagnosis values can be created for rich-lean and for lean-rich transitions. From the diagnosis values for rich-lean and lean-rich transitions interventions in the mixture scattering of the combustion engine 1 can be calculated, which compensate the effect of an asymmetrical slowdown of the exhaust gas probe on the pollutant emission of the combustion engine 1.

The invention claimed is:

1. A procedure for diagnosing the increasing speed and the dead time of an exhaust gas probe, which is arranged in the exhaust gas duct of a combustion engine, whereby the diagnosis is carried out due to a comparison of a modeled and a measured signal after a default change of a fuel air ratio of an air fuel mixture that is supplied to the combustion engine and whereby the signal is an output signal of the exhaust gas probe or a modeled or measured signal that is derived from the output signal wherein a first extreme value is determined in the course of the modeled signal and in that a first point of time and a first starting value are determined if the modeled signal deviates by a default amount from the first extreme value, in that a second extreme value in the course of the measured signal is determined and in that a second point of time and a second starting value are determined, if the measured signal deviates from the second extreme value by a pre-determined amount, in that a first integral is created over a pre-determined period of time, beginning at the first point of time above the different between the first starting value and the modeled signal, and in that a second integral is created over a second period of time, beginning at the second point of time, above the difference between the second starting value and the measured signal, in that the second period of time is equal to the pre-determined period of time or in that the end of the second period of time related to the point of time of the change of the fuel air ratio or related to a first point of time is determined and in that from a quantitative comparison between the first integral and the second integral a quantitative comparative value is created, which indicates the increasing speed and/or the dead time of the exhaust gas probe.

2. The procedure according to claim 1, wherein the quantitative comparative value is determined by creating a difference or a quotient between the first integral and the second integral or between the second integral and the first integral.

3. The procedure according to claim 1, wherein the second pre-determined period of time is provided depending on operating parameters of the combustion engine.

4. The procedure according to claim 1, wherein the end of the second period of time related to the point of time of the change of the fuel air ratio or related to the second point of time is determined depending on operating parameters of the combustion engine.

5. The procedure according to claim 1, wherein the increasing speed and the dead time are determined are separately evaluated after a change of the fuel air ratio from a lean to a rich mixture and from a rich to a lean mixture.

6. The procedure according to claim 1, wherein a malfunctioning exhaust gas probe is indicated if the quantitative comparative value exceeds or falls below a default first threshold value or if the dead time exceeds a second default threshold value.

7. The procedure according to claim 1, wherein a malfunctioning exhaust gas probe is indicated if in several consecutive determinations the quantitative comparative value or the average value of the quantitative comparative value exceeds or falls below the default first threshold value or if the dead time or the average value of the dead time exceeds the default second threshold value.

8. The procedure according to claim 1, wherein an interruption of the air fuel mixture is determined at a change of the fuel air ration from a lean to a rich mixture and a change from a rich to a lean mixture and/or from the difference between the amounts of the quantitative comparative values at a change of the fuel air ratio from a lean to a rich mixture or a change from a rich to a lean mixture.

9. The procedure according to claim 8, wherein the air fuel mixture that is supplied to the combustion engine is enriched if the quantitative comparative value of the integrals implies a greater deviation of the integrals at a change of the fuel air ratio from a rich to a lean mixture than at a change of the fuel air ratio from a lean to a rich mixture and in that the air fuel mixture is made lean if the quantitative comparative value of the integrals implies a greater deviation of the integrals at a change of the fuel air ratio from a lean to a rich mixture than at a change of the fuel air ratio from a rich to a lean mixture.

10. The procedure according to claim 1, wherein a wrongly slowed down exhaust gas probe is signalized to the operator of the combustion engine and/or registered in an error memory.

11. The procedure according to claim 1, wherein the evaluation takes place on the basis of the inverted lambda signal of a wide band lambda probe.

12. An application of the procedure according to claim 1 for the diagnosis of a wide band lambda probe or for the diagnosis of a nitric oxide sensor.

13. A procedure for determining the dead time of an exhaust gas probe, which is arranged in an exhaust gas duct of a combustion engine, wherein the diagnosis is carried out due to a diagnosis of a comparison of a modeled and a measured signal after a default change of a fuel air ratio of a air fuel mixture that is supplied to the combustion engine and wherein the signal is an output signal of the exhaust gas probe or a modeled or measured signal that is derived from the output signal, is thereby characterized, in that a first extreme value is determined in the course of the modeled signal and in that a first point of time and a first starting value are determined if the modeled signal deviates by a default amount from the first extreme value, in that a second extreme value in the course of the measured signal is determined and in that a second point of time and a second starting value are determined, if the measured signal deviates from the second extreme value by a pre-determined amount, and in that the dead time of the exhaust gas probe is determined from the difference between the second point of time and the first point of time.

14. A device for diagnosing the increasing speed and the dead time of an exhaust gas probe, which is arranged in an exhaust gas duct of a combustion engine, with a calculation model for calculating a modeled signal and measuring means for determining a measured signal, whereby the signal is a modeled or measured output signal of the exhaust gas probe or a model or measured signal that is derived from the output signal, with a comparing unit for comparing the modeled signal with the measured signal for diagnosing the increasing speed and the dead time of the exhaust gas probe after a default change of a fuel air ratio of an air fuel mixture that is supplied to a combustion engine, wherein a tracker is provided for determining a first extreme value, a first starting value and a first point of time in the course of the modeled signal, in that a second tracker is provided for determining a second extreme value, a second starting value and a second point of time in the course of the measured signal, in that a first integrator is provided for creating a first integral by integrating the difference of the modeled signal to the first starting value, beginning at the first point of time, over a pre-determined period of time, and in that a second integrator is provided for creating a second integral by integrating the difference of the measured signal to the first starting value, beginning at the second point of time over a second period of time and in that the first point of time and the second point of time as well as the first integral and the second integral are supplied to the comparing unit.

15. The device according to claim 14, wherein the function of the calculation model, the trackers, the integrators and the comparing unit are construed as soft- and/or hardware solution within a motor electronic.

* * * * *

UNITED STATES PATENT AND TRADEMARK OFFICE
CERTIFICATE OF CORRECTION

PATENT NO. : 8,245,566 B2
APPLICATION NO. : 12/571587
DATED : August 21, 2012
INVENTOR(S) : Wehmeier et al.

It is certified that error appears in the above-identified patent and that said Letters Patent is hereby corrected as shown below:

Col. 10, line 42, claim 1: "above the different between" should read --above the difference--

Col. 11, line 17, claim 8: "fuel air ration from" should read --fuel air ratio from--

Signed and Sealed this
Nineteenth Day of March, 2013

Teresa Stanek Rea
*Acting Director of the United States Patent and Trademark Office*